United States Patent [19]

Kampe et al.

[11] Patent Number: 5,795,899

[45] Date of Patent: Aug. 18, 1998

[54] SOLUBLE SALTS OF 4-AMINO-2-(4,4-DIMETHYLIMIDAZOLIDIN-2-ON-1-YL) PYRIMIDINE-5-CARBOXYLIC ACID N-METHYL-N-(3-TRIFLUOROMETHYLPHENYL)-AMIDE, A PROCESS FOR THE PREPARATION THEREOF, THE USE THEREOF AS PHARMACEUTICALS AND STARTING MATERIALS

[75] Inventors: Klaus-Dieter Kampe, Bad Soden am Taunus; Ernold Granzer, Kelkheim; Michael Leineweber, Frankfurt am Main; Manfred Hüttinger, Wien, all of Germany

[73] Assignee: Hoechst Aktiengesellschaft, Frankfurt am Main, Germany

[21] Appl. No.: 394,521

[22] Filed: Feb. 23, 1995

Related U.S. Application Data

[63] Continuation of Ser. No. 16,527, Feb. 11, 1993, abandoned.

[30] Foreign Application Priority Data

Feb. 22, 1992 [DE] Germany .................. 42 05 483.4

[51] Int. Cl.[6] ............... C07D 403/02; A61K 31/505
[52] U.S. Cl. ............................... 514/275; 544/325
[58] Field of Search .................. 544/325; 514/275

[56] References Cited

U.S. PATENT DOCUMENTS

| | | | |
|---|---|---|---|
| 4,285,946 | 8/1981 | Kampe et al. | 424/251 |
| 4,705,792 | 11/1987 | Granzer et al. | 514/275 |
| 5,571,816 | 11/1996 | Kampe | 514/275 |

FOREIGN PATENT DOCUMENTS

| | | |
|---|---|---|
| 0012361 | 6/1980 | European Pat. Off. |
| 0206297 | 12/1986 | European Pat. Off. |

*Primary Examiner*—John M. Ford
*Attorney, Agent, or Firm*—Finnegan, Henderson, Farabow, Garrett & Dunner, L.L.P.

[57] ABSTRACT

Soluble salts of 4-amino-2-(4,4-dimethylimidazolidin-2-on-1-yl)pyrimidine-5-carboxylic acid N-methyl-N-(3-trifluoromethylphenyl)amide, a process for the preparation thereof, the use thereof as pharmaceuticals and starting materials.

Salts, which are soluble and freely soluble in water, of 4-amino-2-(4,4-dimethylimidazolidin-2-on-1-yl)pyrimidine-5-carboxylic acid N-methyl-N-(3-trifluoromethylphenyl)-amide and a process for the preparation thereof are described. The compounds are suitable for the treatment of lipid metabolism disorders which are beneficially influenced by stimulation of the hepatic LDL receptor.

Also described are the compounds of the formula IV

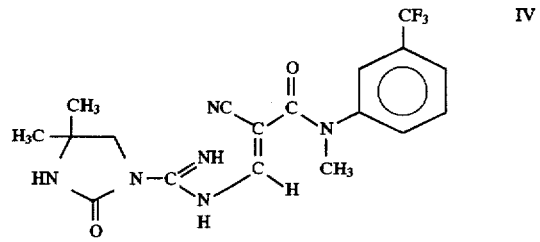

and the salts thereof.

3 Claims, 3 Drawing Sheets

SOLUBLE SALTS OF 4-AMINO-2-(4,4-DIMETHYLIMIDAZOLIDIN-2-ON-1-YL) PYRIMIDINE-5-CARBOXYLIC ACID N-METHYL-N-(3-TRIFLUOROMETHYLPHENYL)-AMIDE, A PROCESS FOR THE PREPARATION THEREOF, THE USE THEREOF AS PHARMACEUTICALS AND STARTING MATERIALS

This is a continuation of application Ser. No. 08/016,527 filed Feb. 11, 1993, now abandoned.

DESCRIPTION

The invention relates to salts, which are soluble and freely soluble in water, of 4-amino-2-(4,4-dimethylimidazolidin-2-on-1-yl)pyrimidine-5-carboxylic acid N-methyl-N-(3-trifluoromethylphenyl)amide. The invention particularly relates to the monohydrochloride of the above-identified pyrimidine derivative.

The use of 4-amino-2-ureidopyrimidine-5-carboxylic acid N-phenylamides for the treatment of obesity and of lipid metabolism disorders has already been described (compare Europ. Patent B-0 012 361 (U.S. Pat. No. 4,285, 946). In addition, the use of a group of these compounds which is specific with respect to its structure, namely corresponding N-(3-trifluoromethylphenyl)amides, for prophylaxis against and treatment of thromboses has been described [compare Europ. Patent B-0 206 297 (U.S. Pat. No. 4,705,792)].

When these compounds are used as pharmaceuticals, their slight solubility in water and in physiologically tolerable solvents or solvent mixtures, including mixtures of such solvents with water, has a disadvantageous effect to a certain extent. This disadvantage has been observed, in particular, with the preferred compounds which have a very beneficial effect on lipid metabolism according to EP-B-0 012 361 and with compounds with high antithrombotic activity (compare EP-B-0 206 297).

It has now been found, surprisingly, that 4-amino-2-(4,4-dimethylimidazolidin-2-on-1-yl)pyrimidine-5-carboxylic acid N-methyl-N-(3-trifluoromethylphenyl)amide of the formula I

I in the form of certain salts formed with moderately strong and strong acids is freely soluble or soluble in water. The invention therefore relates to physiologically tolerated salts, which are soluble and freely soluble in water, of the compound of the formula I.

Salts which are freely soluble in water are to be understood according to the definition in the "Deutsches Arzneibuch" (9th edition 1986, official edition, Deutscher Apotheker-Verlag Stuttgart), page 19, as those for which one part by mass of the relevant salt of the compound I dissolves in 1–10 parts by mass (=parts by volume) of water. Soluble salts are to be understood according to the abovementioned DAB definition as those for which one part by mass of the relevant salt of the compound I dissolves in 10–30 parts by mass of water.

Unless otherwise indicated, the term "freely soluble salts" in the following statements also includes "soluble" salts according to this definition.

This very advantageous property, the good solubility in water of salts of the abovementioned compound I, is exceptionally surprising because both salts and the free bases of compounds which have an analogous structure but have no methyl group on the amide nitrogen atom are exceptionally slightly soluble in water. Thus, for example, only a 0.93× $10^{-3}$ molar solution of the hydrochloride of 4-amino-2-(4,4-dimethylimidazolidin-2-on-1-yl)pyrimidine-5-carboxylic acid N-methyl-(3-trifluoromethylphenyl)amide can be prepared in water at 23° C., which means that 1 part by mass of this compound dissolves in 2500 parts of water. Compound I in the form of the free base is, like 4-amino-2-(4,4-dimethylimidazolidin-2-on-1-yl)pyrimidine-5-carboxylicacid N-(3-trifluoromethylphenyl)amide also in the form of the free base, likewise exceptionally slightly soluble in water.

Because of these properties and of the sparing solubility which is generally to be found for the compounds described in European Patent 0 012 361, both of the free compounds and of the salts in water, it was by no means to be expected that salts of the N-methyl compound I are soluble or freely soluble in water.

The sharp improvement in the solubility of salts of the compound I in water is also surprising because the particular structural feature of the compound I, namely the replacement of the hydrogen atom on the amide nitrogen atom by a methyl group, comprises the introduction of a radical which is more lipophilic than hydrogen. This exchange—of hydrogen by methyl—means that a potential hydrogen bonding disappears in the structure. The structure of the compound I ought accordingly to become less polar. This in turn ought by no means to lead to an improvement in the solubility of the salts in water. It is known that secondary amide groups (with the structural unit HN—CO) show a great tendency to form hydrogen bonds, which as a rule lead to substances which are polar and, as a consequence thereof, tend to be more hydrophilic. In the case of the compound I compared with analogous compounds with a secondary amide group, surprisingly the reverse effect occurs, in that in this case substances with pronounced hydrophilicity are produced by salt formation with the compound I containing a tertiary amide group.

The good solubility in water of salts of the compound I has some significant advantages for the compound I when used as pharmaceutical. The salts of the compound I which are freely soluble in water have, because of this property, a beneficial effect on the absorption of this active substance by the body of the individual to be treated. Accordingly, there is also a beneficial effect on the bioavailability of the active substance in the relevant body.

The good solubility in water also has particular advantages for the pharmaceutical formulations of this active substance. It is known that active substances which form freely water-soluble salts can be pharmaceutically manipulated and processed more straightforwardly and reliably than slightly soluble or virtually water-in-soluble compounds. Viewed overall, many problems relating to the formulation and the use of the compound I as medicinal substance are simplified. Furthermore, a water-soluble medicinal substance, such as the salts of the compound I which are freely soluble in water, is easier and safer to use, for example also with regard to dosage.

The following Table 1 lists, for the purpose of comparison, solubilities in water of salts of similar compounds which are not methylated on the amide nitrogen atom. As is evident from Table 1, the salts of the listed N-dimethyl compounds (Nos. 1–11) with different substitution patterns are all slightly and very slightly soluble in water, except for the compound No. 6 which is sparingly soluble in water.

Table 2 shows the solubilities of the salts, according to the invention, of the compound I which are, by contrast, soluble and freely soluble in water.

Preferred salts of the compound of the formula I are the hydrochloride, hydrobromide, nitrate, hydrogen (R,R)-tartrate and the p-toluenesulfonate, especially the hydrochloride.

BRIEF DESCRIPTION OF THE DRAWINGS

The Northern blot technique was used to determine the relative LDL receptor MRNA levels. The LDL receptor MRNA level is increased about 2.5-fold after six hours.

The LDL receptor MnRNA levels in the human hepatocytoma cell line HepG2 and in rat livers are increased 2 to 2.5-fold within a few hours after administration of the hydrochloride of the compound I.

Lipoprotein-deficient serum (LPDS) was in this case prepared by ultracentrifugation by a standard process (Goldstein, J. L., Basu, S. K and Brown, M. S., Methods Enzymol. 98, 241 (1983)). The MRNA in the serum was prepared in analogy to the method described above. The LDL receptor mRNA stimulation does not depend on the cholesterol "supply level", as was shown by incubation of the cell line in whole serum and in lipoprotein-deficient (LDL-deficient) serum.

FIG. 3 shows that the increased MnRNA synthesis also leads to a corresponding increase in the fimctional LDL receptor levels on HepG2 cells. The uptake of $^{125}$I-labeled homologous LDL is increased by up to two and a half times. In this test, homologous LDL which had been purified by standard processes was labeled with $^{125}$I by the iodine monochloride method. Used in this case was the method of Bilheimer which is disclosed in the literature and is a modification of the iodination technique originally developed by McFarlaine (compare Bilheimer, D. W., Eisenberg, S., and Levy, R. L., Biochim. Biophys. Acta, 260, 212 (1972)).

TABLE 1

Solubility of salts of some of the compounds which are described or mentioned in European Patents 0 012 361 and 0 206 297 and are N—H analogs of the compound I in water

| No. | R$^1$ | R$^2$ | R$^4$ | R$^5$ | Salt | Temp. [°C.] | Molarity × 10$^{-3}$ | Concentration in % by weight | 1 part by mass dissolves in . . . parts of H$_2$O |
|---|---|---|---|---|---|---|---|---|---|
| 1 | CH$_3$ | H | H | H | * | 25.0 | 0.93 | 0.04 | 2500 |
| 2 | CH$_3$ | H | H | H | # | 23.0 | 0.90 | 0.08 | 1250 |
| 3 | CH$_3$ | H | H | F | * | 26.2 | 3.17 | 0.14 | 703 |
| 4 | CH$_3$ | H | Cl | H | * | 25.1 | 9.91 | 0.46 | 217 |
| 5 | CH$_3$ | H | H | Cl | * | 25.2 | 2.03 | 0.10 | 1055 |
| 6 | CH$_3$ | H | OCH$_3$ | H | * | 24.1 | 28.94 | 1.32 | 75 |
| 7 | CH$_3$ | H | H | OCH$_3$ | * | 24.5 | 3.92 | 0.18 | 554 |
| 8 | C$_3$H$_7$ | H | Cl | H | * | 24.2 | 2.59 | 0.13 | 781 |
| 9 | C$_3$H$_7$ | H | H | Cl | * | 24.2 | 2.80 | 0.13 | 725 |
| 10 | C$_3$H$_7$ | H | H | H | * | 25.7 | 8.54 | 0.39 | 255 |
| 11 | H | CH$_3$ | H | H | * | 25.8 | 8.38 | 0.36 | 277 |

* = hydrochloride
# = sulfate

TABLE 2

Solubility of salts, according to the invention, of the compound I and of the compound I in water

| Compound | | Temp. [°C.] | Concentration in % by weight | 1 part by mass dissolves in ... parts of $H_2O$ |
|---|---|---|---|---|
| A. Salts of the compound I | 1. Hydrochloride | 25.0 | 43.0 | 1.33 |
| | 2. Nitrate | 23.5 | 11.0 | 8.13 |
| | 3. p-Toluenesulfonate | 23.2 | 6.5 | 14.44 |
| | 4. Hydrogen (R,R)-tartrate | 24.6 | >9.1 | <9.90 |
| B. Compound I (free base) | — | 24.8 | 0.08 (molarity:2.0 ×10⁻³) | 1220 |

The invention furthermore relates to a novel process for the preparation of 4-amino-2-(4,4-dimethylimidazolidin-2-on-1-yl)pyrimidine-5-carboxylic acid N-methyl-N-(3-trifluoromethylphenyl)amide of the formula I and of its freely water-soluble salts, which comprises cyclizing a compound of the formula IV

IV or a salt or a salt mixture of this compound at a temperature of 0° to 240° C. with or without added solvent to give the compound of the formula I or a salt or a salt mixture of this compound, converting a resulting compound of the formula I where appropriate into a salt which is soluble or freely soluble in water, or converting a resulting salt or salt mixture where appropriate into a salt which is soluble or freely soluble in water.

The guanidine derivative of the formula IV is a novel compound. The invention therefore also relates to the compound of the formula IV in the form of both possible stereoisomers, the E and the Z form, and to the acid addition salts thereof.

The invention furthermore relates to a process for the preparation of the compound of the formula IV or of the salts thereof, which comprises reacting a compound of the formula II

II or a salt of this compound with a compound of the formula III

III in which $R^6$ is $C_1$–$C_4$-alkyl, in the presence of an organic solvent or diluent to form the compound of the formula IV or a salt of this compound, and converting the resulting compound of the formula IV where appropriate into a salt, or converting a resulting salt where appropriate into the compound of the formula IV.

The compound IV is usually obtained as a mixture of stereoisomers (E and Z). It may, however, also be formed as pure stereoisomer (E or Z form). The compound IV and the salts thereof are used as starting material for the preparation of the compound I and of the soluble and freely water-soluble salts. As a monoacidic base, the compound IV forms acid addition salts. In principle, all protic acids are suitable for the formation thereof; strong to moderately strong acids are advantageously employed for the salt formation. Examples which may be mentioned are the following: hydrochloric, hydrobromic or hydroiodic acid, sulfuric, phosphoric, nitric or perchloric acid, ($C_1$–$C_4$)-alkanephosphonic acids, sulfonic acids such as methane-, benzene-, toluene- or trifluoromethanesulfonic acid, sulfamic acid, monomethyl sulfate, acetic, chloroacetic, dichloroacetic, trichloroacetic or trifluoroacetic acid, formic, propionic, oxalic, malonic, maleic, succinic, glutaric, malic, tartaric, citric, fumaric, lactic, glycolic or pyruvic acid, benzoic or benzoic acids which are substituted in the phenyl radical, such as toluylic acid or p-nitrobenzoic acid or salicylic acid, furancarboxylic and/or mandelic acid.

The compound II which is required as starting material for the preparation of the compound IV is known. The compounds of the formula III can be prepared by the methods known for this enol ether type, starting from the known 3-methylaminobenzotrifluoride (Angew. Chemie Suppl. 1982, 1213).

In the case where the compound II is used in the form of a salt, an advantageously equimolar amount of a basic compound is additionally used in the reaction with a compound of the formula III.

A salt of the compound II means acid addition salts to be obtained with inorganic and with organic acids. Preferred salts of the compound II are the hydrobromide, hydrochloride or the sulfate. The hydrobromide and/or hydrochloride are particularly suitable for the process according to the invention.

The reaction of the amidinoimidazolidinone of the formula II with a compound of the formula III can take place under a wide variety of conditions. This applies both to the reaction temperature and to the solvents or diluents which are also used where appropriate. Thus, the reaction according to the invention of the compound II with a compound III can take place at a temperature of −100° C. to +200° C. with or without the addition of a solvent or diluent. This reaction is expediently carried out at from −30° C., preferably +10° C., to +100° C., preferably +35° C., in the presence of solvents or diluents.

Solvents or diluents which can be used are, in principle, all solvents which are (substantially) inert to the compounds II and III, including water. Advantageously used as solvents or diluents are $C_1$–$C_5$-alcohols, tetrahydrofuran, dioxane, lower aliphatic ethers such as diethyl, methyl t-butyl and diisopropyl ethers, acetonitrile, N,N-dimethylformamide, N,N-dimethylacetamide, lower di- and monoethers of glycol and diglycol, such as 1,2-dimethoxyethane, methylglycol, ethylglycol, diglycol dimethyl and monomethyl ethers, ethyl acetate, methyl acetate, toluene, pyridine, acetone, chloroform and/or dichloromethane. Preferred solvents and diluents are $C_2$–$C_4$-alcohols, tetrahydrofuran, dioxane, 1,2-dimethoxyethane, methyl t-butyl ether and/or acetonitrile. It is also possible to use mixtures of the solvents listed, as well as mixtures of those listed with other solvents.

It is possible in the reaction according to the invention of the compound II with a compound III for the (stoichiometric) ratios of the amounts in which these compounds are used to vary within a wide range. II and III can be reacted together in equivalent or in non-equivalent amounts. The latter means that one of the two compounds can be used in a stoichiometric excess. The compound II is preferably reacted as base with III in equivalent amounts or in a ratio whereby the compound III is present in a stoichiometric excess. If the compound II is used as acid addition salt, it can also be employed in a stoichiometric excess relative to III.

The necessary reaction times depend on the temperature at which the reaction is carried out. They can vary within a wide range. As a rule, the reaction times when temperatures of +10° C. to +60° C. are used are 0.3–10 hours, with the reaction times being—as is known—inversely related to the temperature.

If the compound II is used in the form of a salt, a basic compound is added—expediently in equimolar amount—in the reaction according to the invention, or the basic compound II is, before the addition of a compound III, partially or completely liberated from its salt with a basic compound. The basic compound which is also used for this purpose is preferably allowed to act on the salt which is used of the amidinoimidazolidinone II before addition of a compound of the formula III. The reaction according to the invention can thus also be carried out as a "one-pot reaction" in this embodiment. Basic additives which can be used are inorganic and/or organic basic compounds. Examples which may be mentioned are: alkali metal or alkaline earth metal alcoholates of lower alcohols, alkali metal or alkaline earth metal hydroxides or hydrides, as purely organic bases tertiary amines such as lower trialkylamines and/or N,N-dimethylaniline, diazabicycloundecene (DBU) and analogous cyclic (trisubstituted) amidines, tetraalkylammonium hydroxides, 2- or 4-dialkylaminopyridines and/or diazabicyclo[2.2.2]octane (Dabco).

Alkali metal alcoholates of ($C_1$–$C_3$)-alkanols, sodium hydride, DBU and DBU-analogous amidines or tetramethylammonium hydroxide are preferably used as basic additives, and sodium or potassium methylate and/or ethylate are particularly suitable.

An advantageous embodiment of the process according to the invention therefore comprises reacting the compound of the formula II in dissolved form at a temperature of 10° C. to 35° C. with a compound of the formula III in which $R^6$ has the abovementioned meaning, with $R^6$ preferably being methyl or ethyl. After a reaction time of 0.3–4 hours, the compound of the formula IV which has been formed and which usually separates out as slightly soluble crystals is isolated by filtration and dried at a temperature of 10° C. to 35° C.—expediently under vacuum.

It was surprising, knowing what is disclosed in the European patents cited in the introduction, that on reaction of compound II with a compound III it is possible to isolate the compound IV as crystalline solid in high yields and high purity.

No compounds of the type of the compound IV were observed in the preparation of the compounds described in European Patent 0 012 361. The stability of the compound IV is particularly surprising and makes it possible conveniently to isolate this compound, which is required as starting material for the process according to the invention, in good yields.

The isolation of the compound of the formula IV is possible with ease because of the general slight solubility of this compound, especially in organic solvents suitable for the process according to the invention.

Since the compound IV is for the purpose of the present invention reacted to give the final product of the formula I or the freely soluble salts of this compound I, it is not absolutely necessary to isolate the compound IV or the salts in pure form. On the contrary, the cyclization can be carried out with modification of the reaction conditions as a one-pot reaction.

The cyclization of the compound IV as base can take place with or without addition of a solvent or diluent. The cyclization in the presence of solvents or diluents is carried out at a temperature between 0° C., preferably 40° C., and 130° C., preferably 95° C. The cyclization without added solvent or diluent is carried out at a temperature of 60° C., preferably 160° C., to 240° C., preferably 200° C.

If the compound IV is cyclized as base to form the compound I, then one embodiment comprises heating the compound, which is expediently dried, of the formula IV at a temperature of 160° C. to 200° C. for 3–27 minutes—preferably 10–20 minutes—and then immediately cooling to room temperature. The compound I which is formed from IV by thermal cyclization is then isolated. This usually entails removal of two by-products which have also been produced in trace amounts, 3-methylaminobenzotrifluoride (formula V in reaction scheme I) and the compound of the formula VI (compare scheme I). The compound VI can easily be removed because of its solubility in dilute aqueous alkalis, and the compound of the formula V mostly because of its greater volatility by distillation, from the compound I. Complete removal of the compound V from the compound I is possible simply by crystallization and/or by washing the crystalline compound I with solvents in which the compound I is slightly, and the compound V is freely, soluble.

The cyclization of the compound IV in the form of an acid addition salt is preferably carried out also using solvents or diluents at a temperature from 0° C., preferably 45° C., to 150° C. preferably 95° C. This cyclization of a salt of the compound IV can, however, also be carried out without the addition of a solvent or diluent at a temperature from 60° C., preferably 160° C., to 240° C., preferably 200° C.

It is possible to use for this type of cyclization of the compound IV, with or without added solvent, defined acid addition salts which have been prepared separately from the compound IV, as well as mixtures composed of the compound IV and of one or more acids. All compositions can be used for such mixtures, starting with minimal amounts of acid equivalents, for example less than $10^{-4}$ equivalents, up to 2 acid equivalents or more; 0.8–1.6 acid equivalents are preferably used. In the extreme case, the cyclization of the compound IV can be carried out in an acid which acts simultaneously as solvent or diluent. This embodiment is preferred when formic, acetic and/or propionic acid are used as acids and as diluent. Thus, it is not absolutely necessary to employ defined, separately prepared salts for the cyclization of acid addition salts of the compound IV to form the compound I.

The cyclization of the compound IV with the addition of one or more acids in the presence of solvents or diluents is a very suitable embodiment of the process according to the invention.

An advantageous embodiment of the cyclization of salts of the compound IV or the cyclization of the compound IV with the addition of one or more acids comprises heating the compound IV with the addition of 0.2 to 2.5 or more—preferably 1 to 1.5—acid equivalents in the presence of a solvent or diluent at a temperature of 25° C., preferably 45° C., to 120° C., preferably 95° C. The reaction times in this case are 0.5–9 hours, depending on the temperature. It is subsequently possible by adding suitable solvents in which the appropriate salt of the compound I which has been formed is slightly soluble to deposit the salt as crystals. Simple and efficient removal of the compound I which has been formed from by-products which have also been produced is possible in this way (compare reaction scheme I in this connection).

All protic acids can be used in principle for the carrying out which is described above of the cyclization of the compound IV. The following examples may be mentioned: hydrochloric, hydrobromic, hydrofluoric or hydroiodic acid, sulfuric, phosphoric, polyphosphoric, nitric or perchloric acid, ($C_1$–$C_4$)-alkanephosphonic acids, sulfonic acids such as methane-, benzene-, toluene- or trifluoromethanesulfonic acid, sulfamic acid, monomethyl sulfate, acetic, cyanoacetic, chloroacetic, dichloroacetic, trichloroacetic or trifluoroacetic acid, formic, propionic, oxalic, malonic, maleic, succinic, glutaric, malic, tartaric, citric, fumaric, lactic, glycolic or pyruvic acid, benzoic or benzoic acids substituted in the phenyl radical, such as toluylic acid or p-nitrobenzoic acid or salicylic acid, furancarboxylic and/or mandelic acid.

Acetic, oxalic, tartaric, formic, citric, malic, fumaric, dichloroacetic, trichloroacetic and/or propionic acid are preferably used.

Acetic, oxalic, tartaric, formic and/or citric acid are particularly suitable.

Suitable solvents or diluents for this carrying out of the cyclization of the compound IV in the form of salts or salt mixtures are in principle all organic solvents which are inert to the compound IV, and/or water. Preferably used are $C_1$–$C_4$-alcohols, tetrahydrofuran, dioxane, methyl t-butyl ether, acetonitrile, N,N-dimethylformamide and/or -acetamide, lower glycol di- and monoethers such as 1,2-dimethoxyethane, methyl- and/or ethylglycol, and/or methyl acetate, ethyl acetate, acetone, chloroform, dichloromethane, formic acid and/or acetic acid.

A preferred embodiment of the process according to the invention comprises heating the compound IV in the presence of glacial acetic acid and/or formic acid, with or without the addition of one or more moderately strong to strong acids, at a temperature of 25° C., preferably 45° C., to 120° C., preferably 95° C., for 0.3 to 5 hours. Glacial acetic acid and/or formic acid simultaneously act as solvents in this case and are used in a stoichiometric excess relative to the compound IV. Examples of moderately strong to strong acids which are also used where appropriate and which may be mentioned are oxalic, citraconic, tartaric, citric, trifluoroacetic, cyanoacetic, chloroacetic, dichloroacetic and/or trichloroacetic acid and/or polyphosphoric acid.

If required, the compound I is liberated from the isolated salt in a manner generally known for such base formations and is converted where appropriate by the addition of an appropriate acid into a (different) salt which is soluble or freely soluble in water.

The "acid equivalents" mentioned in connection with the salt formation from compound I relate to the compound I as monoacidic base.

The process according to the invention for the preparation of the compound I is illustrated by the following scheme.

Scheme I

-continued
Scheme I

The 3-methylaminobenzotrifluoride V which is formed as by-product in the cyclization of the compound IV can be isolated and returned to the process for preparing III.

The compound of the formula I and the salts of this compound which are freely soluble in water have valuable pharmacological properties and can therefore be used as pharmaceuticals. They are distinguished, for example, by hypolipidemic properties.

It has been found, surprisingly, that the compound of the formula I and the salts of this compound which are freely soluble in water increase the LDL receptor level. The compound I and the salts thereof which are freely soluble in water are therefore suitable for the treatment of lipid metabolism disorders which can be beneficially influenced by a stimulation of the hepatic LDL receptor. The invention therefore also relates to the use of compound I and of the salts thereof which are freely soluble in water for the treatment of the said lipid metabolism disorders.

The effect is based on a rapid direct stimulation of the LDL receptor (apoB/E receptor) in the liver. Via stimulation of the natural cholesterol catabolism pathway, the compound I and the salts thereof which are freely soluble in water reduce the atherogenic LDL and VLDL. The HMG-CoA reductase inhibitors or ion exchanger resins, by contrast, indirectly stimulate, owing to a reduction in the intracellular cholesterol levels or to an increase in the cholesterol required for the biosynthesis of bile acids, the expression of the LDL receptors on the liver cell. Thus, side effects like those observed with the statins owing to their drastic inhibition of HMG-CoA reductase also in other organs than the liver (for example influence on ubiquinone formation) are not to be expected. Nor have side effects of this type been observed to date. There is no risk of compliance problems like those with the ion exchanger resins, which are caused by the large daily doses of 15 to 30 g required.

Particularly dangerous in atherogenesis are certain cholesterol-transporting lipoprotein fractions such as the small-particle LDL fractions. The catabolism of most of the LDL (75%) is effected by the LDL receptor in the liver. The cholesterol is then partially metabolized in the liver cells to bile acids and excreted in the form of bile, but part of the cholesterol is also directly excreted in the bile. It has thus already been recognized in principle and already demonstrated therapeutically by the substances which have an indirect effect (such as statins) that the LDL receptor is an ideal point of attack for an antiatherosclerotic with hypolipidemic activity in humans.

The compound I and the salts thereof which are freely soluble in water increase the LDL receptor level. The increased LDL (IDL, chylomicron remnant) uptake in the liver cells, brought about by the LDL receptor level increased in this way on the cell surface, then leads to increased hepatic breakdown of LDL cholesterol. The HDL levels are unaffected.

Figure 1:
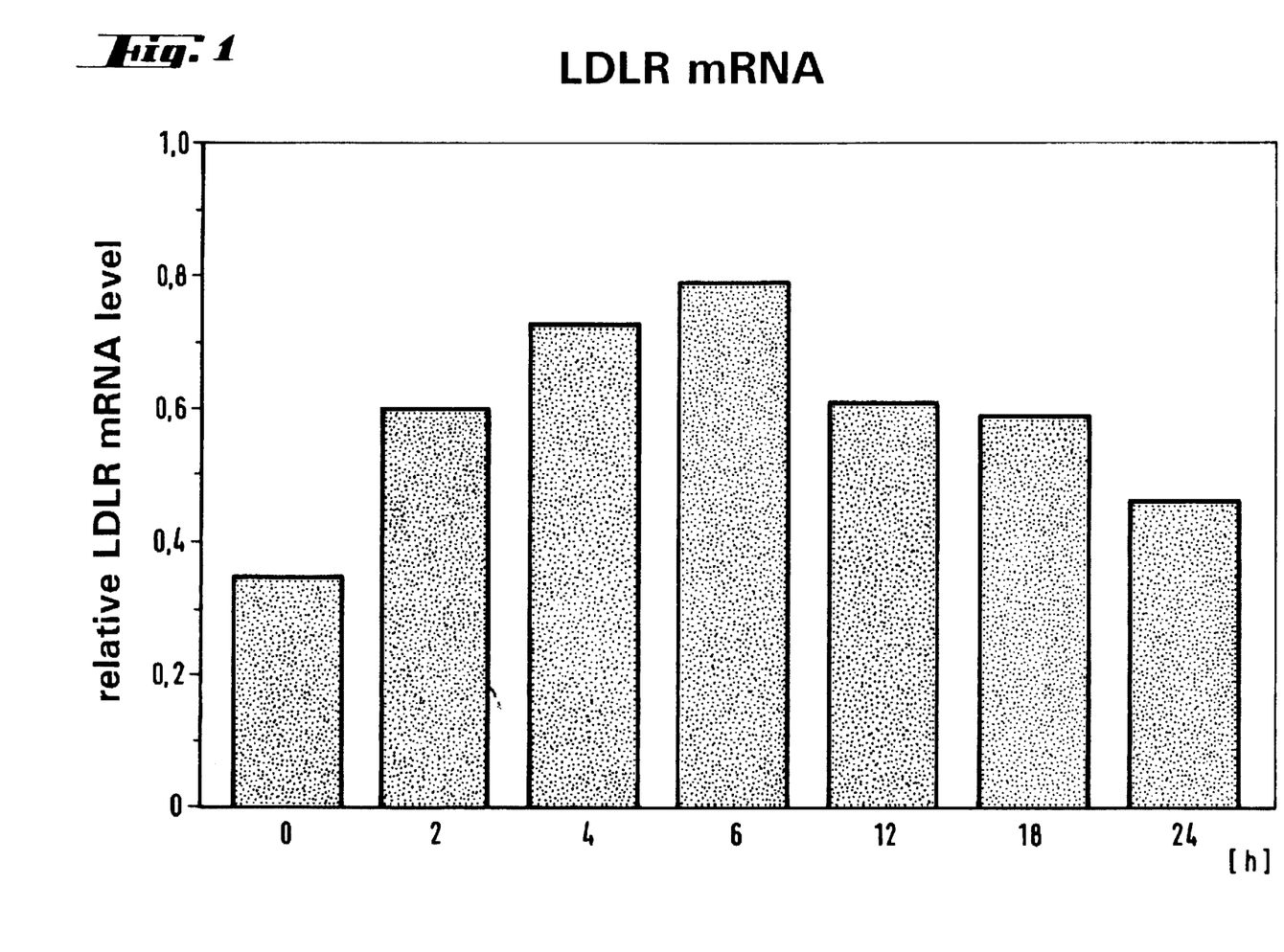
FIG. 1 shows the stimulation of LDL receptor MnRNA expression in vivo in rat livers as a function of the time after administration. Liver tissue was removed at the stated time after a single oral dose of 30 mg/kg of the hydrochloride of compound I and was shock-frozen in liquid nitrogen.
Figure 2:
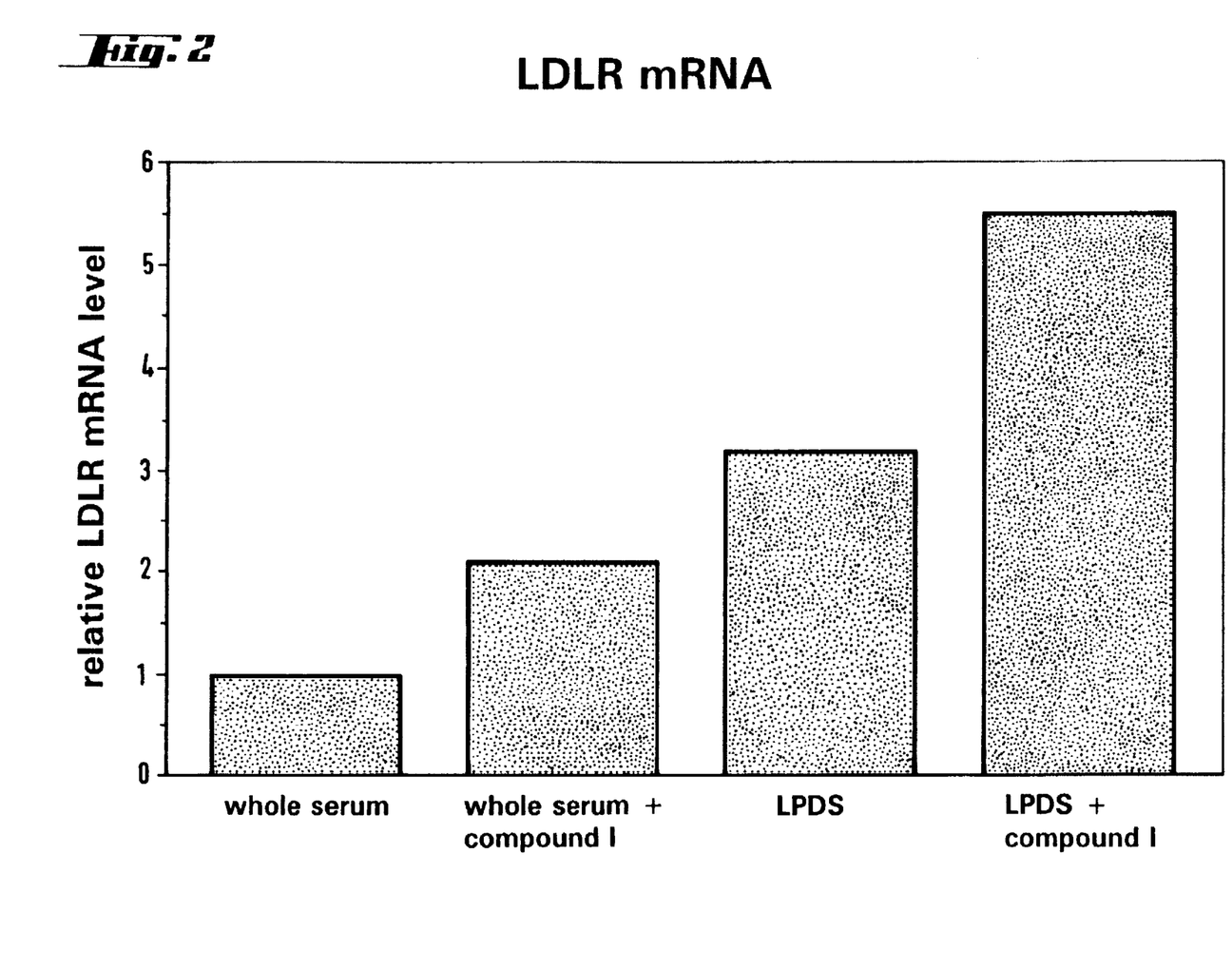
FIG. 2 shows the stimulation of LDL receptor mRNA expression on HepG2 cells in whole serum and in lipoprotein-deficient serum. The HepG2 cells were previously incubated in MEM standard medium which contained 10% fetal calf serum with and without hydrochloride of the compound I ($10^{-6}$M) for 16 hours. Despite the prior stimulation by the dilapidated medium, the LDL receptor MnRNA is over induced by the described compound further by the same factor as was observed on stimulation in whole serum.

The compound of the formula I and the salts which are freely soluble in water thus represent an ideal principle of antiatherosclerotic activity. The following findings demonstrate the mechanism of action which has been found and which makes the described compounds appear particularly suitable for the treatment of those hyperlipidemias which are based on reduced LDL receptor activity:

1. The LDL receptor mRNA levels in the human hepatocytoma cell line HepG2 and in rat livers are increased 2 to 2.5-fold within a few hours after administration of the hydrochloride of the compound I (FIG. 1). The LDL receptor mRNA stimulation does not depend on the cholesterol "supply level", as was shown by incubation of the cell line in whole serum and in lipoprotein-deficient (LDL-deficient) serum (FIG. 2). These observations were made on carrying out the following tests:

The mRNA was prepared by the method described by Chomczynski, P. and Sacchi, N. in Anal. Biochem. 162, 156 (1987). In the case of organs (such as, for example, liver), the deep-frozen tissue was previously homogenized in a mortar on dry ice, and the mRNA was further concentrated by means of oligo dT by standard methods (compare Sambrook, J., Fritsch, E. F. and Maniatis, T., Molecular Cloning, second edition, Cold Spring Harbor (1989); this collection of methods also includes descriptions of all the other relevant standard processes of molecular biology used here). 5 to 20 µm of the dissolved MRNA obtained in this way were denatured by standard processes and fractionated on 1% horizontal agarose gels. The MRNA was transferred by capillary blotting to Hybond N membranes (Amersham). Used as specific hybridization probe was a partial LDL receptor cDNA clone and as internal standard was a plasmid which contained a β-actin gene. Both plasmids were labeled using a random primer kit from Amersham to a specific activity of $5 \times 10^9$ cpm/µg. Prehybridization, hybridization and washing of the filters took place by standard processes. The filters were subsequently exposed on Cronex 4 films (Dupont) in the presence of an intensifying screen at −70° C. overnight or for up to 14 days, and the hybridization signals were quantified from the intensity of blackening of the film using a commercially available laser densitometer. Subsequently, the quotient was determined from the intensity of the LDL receptor band and of the actin band as internal standard to correct for variations in yield.

FIG. 1 shows the stimulation of LDL receptor mRNA expression in vivo in rat livers as a function of the time after administration. Liver tissue was removed at the stated time after a single oral dose of 30 mg/kg of the hydrochloride of compound I and was shock-frozen in liquid nitrogen. Subsequently, the MRNA was prepared as described previously, and the Northern blot technique was used to determine the relative LDL receptor mRNA levels. The LDL receptor mRNa level is increased about 2.5-fold after 6 hours.

FIG. 2 shows the stimulation of LDL receptor mRNA expression on HepG2 cells in whole serum and in lipoprotein-deficient serum. The HepG2 cells were previously incubated in MEM standard medium which contained 10% fetal calf serum with and without hydrochloride of the compound I ($10^{-6}$M) for 16 hours. Despite the prior stimulation by the delipidated medium, the LDL receptor mRNA is overinduced by the described compound further by the same factor as was observed on stimulation in whole serum. Lipoprotein-deficient serum (LPDS) was in this case prepared by ultracentrifugation by a standard process (Goldstein, J. L., Basu, S. K. and Brown, M. S., Methods Enzymol. 98, 241 (1983)). The mRNA in the serum was prepared in analogy to the method described above.

Figure 3:
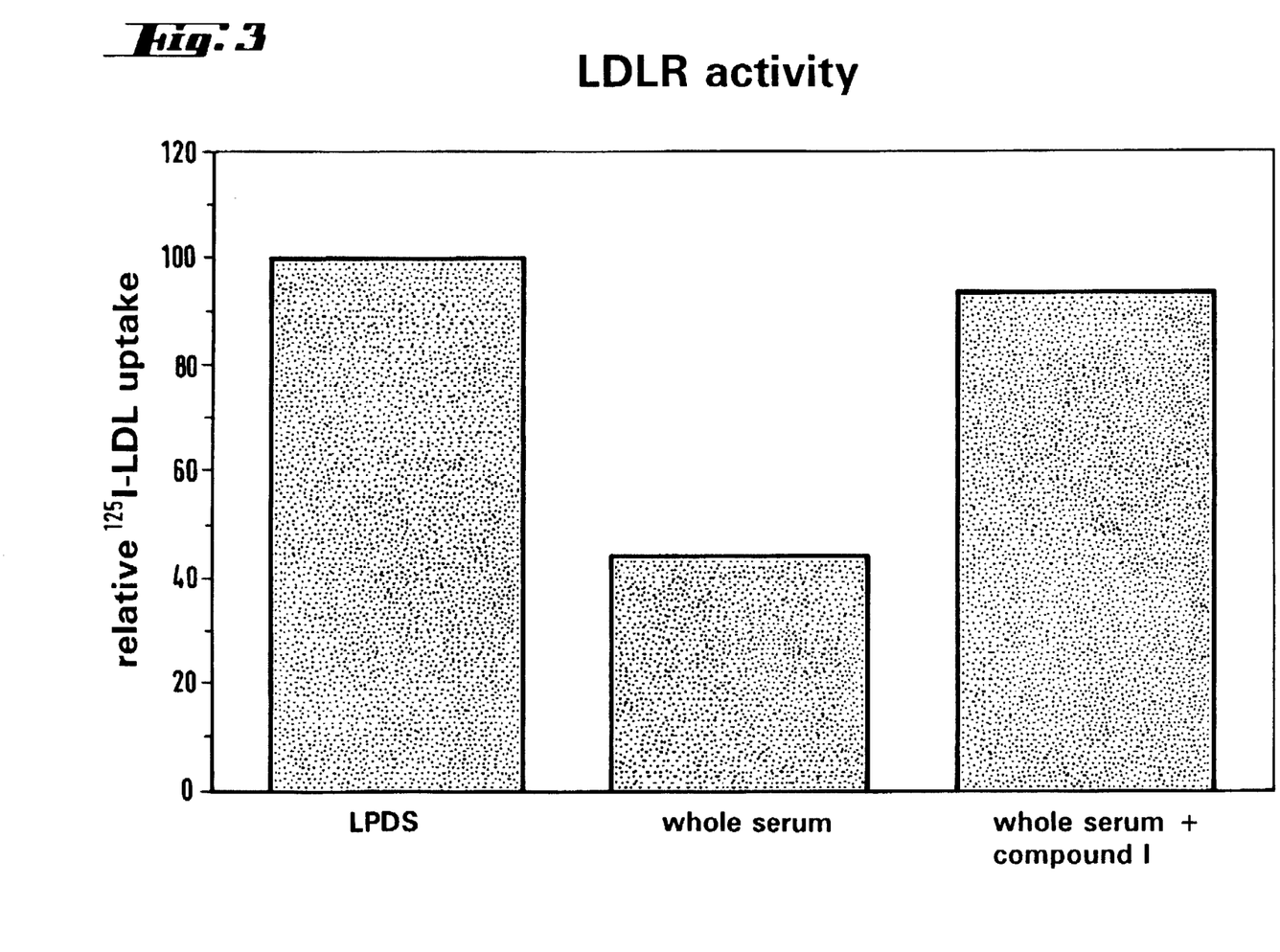

2. The increased mRNA synthesis also leads to a corresponding increase in the functional LDL receptor levels on HepG2 cells. The uptake of $^{125}$I-labeled homologous LDL is increased by up to two and a half times (FIG. 3).

In this test, homologous LDL which had been purified by standard processes was labeled with $^{125}$I by the iodine monochloride method. Used in this case was the method of Bilheimer which is disclosed in the literature and is a modification of the iodination technique originally developed by McFarlaine (compare Bilheimer, D. W., Eisenberg, S., and Levy, R. L., Biochim. Biophys. Acta, 260, 212 (1972)).

To determine the $^{125}$I-LDL incorporation, HepG2 cells were preincubated with and without hydrochloride of the compound I for 36 hours and subsequently incubated with iodine-labeled LDL at 37° C. in an incubator for 3 hours.

Subsequently, the cells were washed in the presence of 2% bovine serum albumin, the cells were lyzed with 1 ml of 0.1N NaOH, and the incorporated radioactivity was measured. The specific radioactivity uptake (total radioactivity uptake less the unspecific radioactivity uptake) per mg of protein was then calculated, as generally customary, via a protein determination by the Lowry method, and the radioactivity taken up by the control serum was set equal to 100%.

3. In the HMG-COA reductase determination in vitro on partially purified HMG-COA reductase from rat liver (compare Avigan J., Bathena, S. J., and Schreiner, M. E., J. Lipid Res. 16, 151 (1975) and Philippi, B. W., and Shapiro, D. J., J. Lipid Res. 20, 588 (1979)), the hydrochloride of compound I does not influence, on addition of $10^{-5}$M, the enzyme activity compared with control incubations (variation 10%), while lovastatin Na (with opened lactone ring) has an $IC_{50}$ of $3 \times 10^{-9}$M in this test.

4. In vivo, the increased LDL receptor activity in experimental animals is reflected by reduction in the lipoprotein fractions which can be metabolized by the LDL receptor (apoB/E receptor), i.e. a reduction in the LDL and VLDL levels is observed. The following tests were carried out:

4.1 Effect on serum lipoproteins of normolipemic male rats in a subchronic test

Groups of in each case 10 male rats of the HOE: WISKf (SPF 71) strain with an initial weight above 180 g received once a day (in the morning) the test product or the comparison product in 1% aqueous ®Tylose MH 300 solution by stomach tube (0.5 ml/100 g of body weight); the control group in each case received only the vehicle. The last (7th) administration took place 24 hours before removal of blood and sacrifice. There was free access to food and water during the test. The food was withdrawn 24 hours before the removal of blood.

The serum from all 10 rats in a group was pooled for the analysis of the serum lipoproteins. The serum lipoproteins were separated with a preparative ultracentrifuge (KONTRON TGA 65, Rotor BECKMAN 50.4 Ti).

The following conditions specified by Koga, S., Horwitz, D. L., and Scanu, A. M., Journal of Lipid Research 10, 577 (1969) and Havel, R. J., Eder, H. A., and Bragdon, H. H., J. Clin. Invest. 34, 1345 (1955) were used to separate VLDL, LDL and HDL:

1. VLDL: Density<1.006, 40,000 rpm for 16 hours
2. LDL: Density 1.006–1.04, 40,000 rpm for 16 hours
3. HDL: Density 1.04–1.21, 40,000 rpm for 18 hours Test kits from BOEHRINGER/Mannheim were used for the enzymatic determination of cholesterol and triglycerides in the separated lipoprotein fractions (compare Siedel, J., Schlumberger, H., Klose, S., Ziegenhorn, J. and Wahlefeld, A. W., J. Clin. Chem. Clin. Biochem. 19, 838 (1981) and Wahlefeld, A. W., in: H. O. Bergmeier: Methoden der enzymatischen Analyse (Methods of Enzymatic Analysis), 2nd edition, Volume II, Verlag Chemie 1974, page 1878). The proteins were determined by the method of Lowry (Lowry, O. H., Roseborough, N. J., Farr, A. L. and R. J. Randell, J. Biol. Chem. 193, 265 (1951)).

The results are compiled in Table 3. Clofibrate was used as comparison product.

TABLE 3

Reduction in the atherogenic serum lipoproteins of male Wistar rats after oral treatment for 7 days
% change compared with control

| Compound | Dose mg/kg/day | TOTAL CHOLESTEROL LDL | PROTEIN VLDL | PROTEIN LDL | TRI-GLY-CER-IDES VLDL |
|---|---|---|---|---|---|
| Compound I* | 30 | −64 | −59 | −52 | −79 |
| Compound I* | 10 | −49 | −52 | −41 | −62 |
| Compound I* | 3 | −32 | −24 | −25 | −25 |
| Compound I* | 1 | −17 | +4 | −15 | +8 |
| Clofibrate | 100 | −31 | −30 | −32 | −34 |

*as hydrochloride 4.2 Effect on hypercholesterolemia in male rats

Groups of in each case 10 male rats of the HOE: WISKf (SPF 71) strain with a weight of about 200 g received each day in the morning a cocktail which contained the substances required to generate a combined dietetic/hormonal hypercholesterolemia, and in each case the product to be tested for the inhibition of hypercholesterolemia, in appropriate dosage. The cocktail was composed of a mixture of 100 g of cholesterol, 30 g of propylthiouracil and 100 g of cholic acid in 1 l of peanut oil. 1 ml of this/100 g of body weight was administered by gavage. The products to be tested were suspended in this cocktail in a concentration such that it contained the daily dose indicated in Table 4 on administration of the amount mentioned above. The other procedure for the treatment and the analysis of the individual parameters were carried out as indicated under 4.1.

Clofibrate was used as comparison product. The results are compiled in Table 4, wherein a) indicates the absolute values and b) indicates the percentage changes.

TABLE 4

Effect on experimental hypercholesterolemia of Wistar rats after oral treatment for 7 days a)

| Compound | Dose mg/kg/day | Total cholesterol (mg/dl) x | Total cholesterol (mg/dl) s | Tri-glycerides (mMol/L) Pool | Lipoprotein fractions 1.006/1.04/1.21 Total cholesterol VLDL | Lipoprotein fractions 1.006/1.04/1.21 Total cholesterol LDL | Lipoprotein fractions 1.006/1.04/1.21 Total cholesterol "HDL" | Protein VLDL | Protein LDL | Protein "HDL" | Tri-glycerides VLDL |
|---|---|---|---|---|---|---|---|---|---|---|---|
| Compound I* | 30 | 137 | 23 | 1.10 | 126 | 369 | 1056 | 1105 | 391 | 4090 | 425 |
| Compound I* | 10 | 556 | 407 | 2.45 | 3088 | 4099 | 508 | 1981 | 1040 | 5004 | 677 |
| Diet control |  | 736 | 176 | 2.92 | 4666 | 4696 | 591 | 2162 | 1242 | 5380 | 1460 |
| Clofibrate | 100 | 880 | 273 | 3.68 | 5924 | 5434 | 648 | 809 | 1435 | 3920 | 1770 | b)

SERUM
% change compared with control at the end of treatment

| Compound | Dose mg/kg/day | Total cholesterol | Tri-glycerides | Total cholesterol VLDL | Total cholesterol LDL | Total cholesterol "HDL" d > 1.04 | Protein VLDL | Protein LDL | Protein "HDL" d > 1.04 | Tri-glycerides VLDL |
|---|---|---|---|---|---|---|---|---|---|---|
| Compound I* | 30 | −81 | −62 | −97 | −92 | +79 | −49 | −68 | −24 | −71 |
| Compound I* | 10 | −24 | −16 | −34 | −13 | −14 | −8 | −16 | −7 | −54 |
| Clofibrate | 100 | +20 | +26 | +27 | +16 | +10 | −63 | +16 | −27 | +21 |

*as hydrochloride 4.3 Effect on carbohydrate-induced hypertriglyceridemia

Groups of in each case 10 male Sprague-Dawley rats (supplied by the breeder Mollegard with a weight of 250–280 g) received on each of 4 consecutive days one administration of the compound dissolved in PEG 400 by gavage. In addition, after the 3rd administration and 8 and 24 hours later they received 2.5 g of fructose/kg, likewise by gavage. Moreover, after the 3rd administration of product, 50% strength fructose solution was offered to them as drinking water ad libitum, and the food was withdrawn.

Retroorbital removal of blood, from which the serum was obtained for the triglyceride determination and VLDL preparation in the ultracentrifuge (flotation at d=1.006), took place 3 hours after the last product/fructose administration. The food received by the animals from 1 week before the 1st administration and up to the 3rd administration was a diet with 40% casein in the feed meal.

The animals develop, as a result of this treatment, a hypertriglyceridemia which approximately corresponds to Fredrickson phenotype IV in humans. The serum triglycerides of the normal animals increased from 0.54 to 1.1 mmol/l, and the VLDL triglycerides from 0.67 to 1.81. As is shown in Table 5, the hydrochloride of the compound I is able to inhibit the increase in the VLDL triglycerides by almost one half with only 1 mg/kg/day. Clofibrate at a dose which is 100 times higher has only a slight inhibitory effect.

The results are compiled in Table 5.

TABLE 5

Inhibition of carbohydrate-induced hypertriglyceridemia after oral treatment for 4 days

| Product | Dose mg/kg/day | TRIGLYCERIDES (mmol/l) in SERUM x | TRIGLYCERIDES (mmol/l) in SERUM s | TRIGLYCERIDES (mmol/l) in SERUM % change from fructose control | in the VDVL fraction Pool n = 10 | in the VDVL fraction % change from fructose control |
|---|---|---|---|---|---|---|
| Animals without fructose |  | 0.54 | 0.10 |  | 0.67 |  |
| Fructose control |  | 1.11 | 0.41 |  | 1.81 |  |
| Compound I* | 30 | 0.29 | 0.06 | −74 | 0.19 | −90 |
|  | 10 | 0.35 | 0.07 | −68 | 0.37 | −80 |
|  | 3 | 0.54 | 0.09 | −51 | 0.69 | −62 |
|  | 1 | 0.71 | 0.19 | −36 | 1.00 | −45 |
| Clofibrate | 100 | 0.83 | 0.49 | −25 | 1.15 | −37 |

*as hydrochloride

The compound of the formula I and the salts which are freely soluble in water are furthermore distinctly superior, by reason of their reduced inhibitory effect on cell proliferation, to the NH analog of compound I, 4-amino-2-(4,4-dimethylimidazolidin-2-on-1-yl)pyrimidine-5-carboxylic acid N-(3-trifluoromethylphenyl)amide (HOE 402, imanixil) and the hydrochloride of this compound, as is shown by the test described hereinafter and the test results:

The reduced inhibitory effect on cell proliferation was tested on exponentially growing animal (mouse leukemia cells, L 1210) and human (bronchial carcinoma cells, A 549; colon carcinoma cells, HT 29) tumor cells. This entailed the tumor cells being incubated in RPMI standard medium with various concentrations of the test substances for 72 hours. Cell incubations only in fresh medium served as control. Incubations were set up in quadruplet. After 65 hours, MTT (3-(4,5-dimethyl-2-thiazolyl)-2,5-diphenyl-2H-tetrazolium bromide), which is reduced by undamaged cells to a red insoluble formazan dye, was added. After incubation for a further 7 to 24 hours, the cell supernatant was carefully removed and the formazan dye in the cells was solubilized by adding DMSO and measured quantitatively by photometry at 492 nm. The ratio of the extinction of the substance incubations to the control incubation was quantified. The coefficient of variation in each incubation series was less than 15%. The following Table 6 indicates the $IC_{50}$ values ($IC_{50}$ [µg/ml] is the concentration of the test substance per ml which is necessary for 50% inhibition) from these investigations. It is evident from this that the compound I as hydrochloride must be given at a considerably higher dose in order to have the same proliferation-inhibiting effect ($IC_{50}$) as imanixil hydrochloride.

TABLE 6

| | MTT ASSAY $IC_{50}$ [µg/ml] | | |
|---|---|---|---|
| Substance | L1210 | HT 29 | A 549 |
| Imanixil hydrochloride | 0.7 | 4.3 | 3.4 |
| Compound I as hydrochloride | 13.4 | >100 | >100 |

The compound I and the salts thereof which are freely soluble in water possess a distinctly reduced proliferation inhibition, compared with HOE 402 and HOE 402 hydrochloride, which distinctly improves the safety margin on massive iatrogenic overdosage with possible reversible leukocyte reduction.

The compound of the formula I can be used as pharmaceutical in the form of its pharmaceutically acceptable acid addition salts—this use form is preferred—or as free base because of their pharmaceutical properties, and it is administered either alone or mixed with suitable excipients and/or compatible diluents and, where appropriate, also with other additives too.

The present invention also relates to pharmaceutical compositions which, besides non-toxic, inert pharmaceutically suitable excipients, contain the active substance according to the invention or are composed of the active substance according to the invention, and to processes for the production of these compositions.

Non-toxic, inert pharmaceutically suitable excipients mean pharmaceutically acceptable, solid, semisolid or liquid diluents, fillers and formulation aids of every type which after mixing with the active substance convert it into a form suitable for administration.

Examples of suitable administration forms of the compound I and of the salts of this compound which are freely soluble in water are tablets, coated tablets, powders, capsules, pills, aqueous solutions, suspensions and emulsions, where appropriate sterile injectable solutions, non-aqueous emulsions, suspensions and solutions, sprays and formulations with protracted release of active substance.

The therapeutically effective compounds should be present in the abovementioned pharmaceutical compositions expediently in a concentration of about 0.1, preferably of 0.5, to 99.0, preferably to 70.0, percent by weight of the complete mixture.

The administration concentrations for solutions and aerosols in the form of spray are generally from 0.1 to 20, preferably 0.5–5, percent by weight.

The abovementioned pharmaceutical compositions may, apart from the said active substance, also contain other pharmaceutical active substances.

The abovementioned pharmaceutical compositions are produced in a conventional way by known methods, for example by mixing the active substance or substances with the excipient or excipients. Suitable tablet compositions are described in Examples 27 and 28.

The present invention also relates to the use of active substances according to the invention and of pharmaceutical compositions which contain the active substance according to the invention in human medicine to prevent, improve and/or cure the abovementioned disorders.

The active substance or the pharmaceutical compositions can be administered orally, parenterally, intraperitoneally and/or rectally.

The compound of the present invention which can be used, for example, as hypolipidemic—preferably its salts—can be used to produce pharmaceutical products which contain an effective amount of the active substance together with excipients and which are suitable for enteral and parenteral administration. Preferably used are tablets or capsules (gelatin capsules) which contain the active substance together with diluents or excipients, for example lactose, dextrose, sucrose, mannitol, sorbitol, cellulose, various types of starch and/or glycine, and lubricants such as diatomaceous earth, talc, stearic acid or the salts thereof, such as magnesium or calcium stearate, and/or polyethylene glycol. Tablets expediently also contain binders such as magnesium carbonate, magnesium aluminum silicate, starch, gelatin, tragacanth or methylcellulose, sodium carboxymethylcellulose and/or polyvinylpyrrolidone and, if necessary, colorants, flavorings and sweeteners. Injectable solutions are preferably isotonic aqueous solutions or suspensions which can be sterilized and can contain ancillary substances such as preservatives, stabilizers, wetting agents and/or emulsifiers, solubilizers, salts to regulate the osmotic pressure and/or buffer substances. The pharmaceutical products according to the invention, which can optionally contain further pharmacologically active substances, are produced, for example, by conventional mixing, granulating and coating processes and contain 0.1% to, preferably, about 80%, preferably about 0.5% to about 65% of the active substance.

Oral administration takes place in pharmaceutically customary compositions, for example in the form of tablets, coated tablets or capsules which, for example, contain per daily dose 5, preferably 20, to 1000 mg, preferably to 200 mg, of the active substance mixed with a conventional excipient and/or constituent, it being possible to give single doses of 5 to 200 mg, preferably once to three times a day.

However, it may be necessary to deviate from the said dosages, specifically depending on the nature and the body weight of the subject to be treated, the nature and the severity of the disorder, the nature of the composition and of the administration of the pharmaceutical, as well as the period or interval over which administration takes place. Thus, it may be sufficient in some cases to make do with less than the abovementioned amount of active substance, whereas in other cases the above-mentioned amount of active substance must be exceeded. Establishment of the optimal dosage and mode of administration of the active substances necessary in each case can easily be carried out by any skilled worker on the basis of his expert knowledge.

The following examples serve to illustrate the invention further but without confining the latter to the products and embodiments describe in the examples.

The melting and decomposition points stated in the following examples are uncorrected.

Thin-layer chromatographies were carried out on precoated silica gel 60, F-254 TLC plates from Riedel-de Haen AG with the mobile phases stated in each case in the examples.

EXAMPLE 1

11.93 g (40 mmol) of 2-cyano-3-ethoxyacrylic acid N-methyl-N-(3-trifluoromethylphenyl)amide (compound III) were added to a stirred suspension of 6.25 g (40 mmol) of 1-amidino-4,4-dimethyl-2-oxoimidazolidine in 120 ml of anhydrous 1,2-dimethoxyethane at 20° C. A solution had been produced after stirring for about 5 min, and from this a crystalline substance separated out, starting after about 12 min. The mixture was stirred at 20°–24° C. for a further 2 hours, and subsequently the solid was filtered off with suction and washed with ether. The filtrate was evaporated in vacuo at <26° C. The crystalline residue (8.1 g) was suspended in 25 ml of ether and, after 20 min, the solid was filtered off with suction. Both the resulting crystalline portions were suspended together in about 200 ml of water, stirred at room temperature for 40 min, filtered off with suction, washed with a little water and dried in vacuo over $P_2O_5$ at 20°–25° C. for 48 hours. In this way, 14.02 g (=85.8% yield) of 1-cyano-1-[N-methyl-N-(3-trifluoromethylphenyl)carbamoyl]-2-[imino(4,4-dimethyl-2-oxo-1-imidazolidinyl)methylamino]ethene (compound IV), melting and decomposition point: 186°–189° C., were obtained. This compound shows a characteristic CN band at 2212 $cm^-$ in the IR spectrum. The resulting product is almost pure according to TLC ($CH_2Cl_2/C_2H_5OH$:10:1) ($R_F$ 0.44±0.01). According to the $^1$H-NMR spectrum, a pure stereoisomer (E or Z) is present.

$C_{18}H_{19}F_3N_6O_2$ (408.40); calculated: C 52.94 H 4.69 F 13.96 N 20.58%; found: C 52.70 H 4.65 F 13.20 N 20.30%

EXAMPLE 2

4.69 g (30 mmol) of 1-amidino-4,4-dimethyl-2-oxoimidazolidine were dissolved at 70° C. in a mixture of 38 ml of 1,2-dimethoxyethane and 45 ml of isopropanol. This solution was cooled to 20° C. and, at 20° C., 9.0 g (30.2 mmol) of 2-cyano-3-ethoxyacrylic acid N-methyl-N-(3-trifluoromethylphenyl)amide were added. The mixture was stirred at 20°–24° C. for 1 hour, and the crystalline precipitate which had separated out was filtered off with suction and washed with ether. The filtrate was processed as described in Example 1. This resulted in a further 0.74 g of crystalline product. This and the major portion previously isolated directly were combined, stirred with water as described in Example 1, again filtered off with suction and dried. 10.76 g (=87.8% yield) of product which, according to TLC, is almost pure compound IV were obtained.

EXAMPLE 3

5.97 g (20 mmol) of 2-cyano-3-ethoxyacrylic acid N-methyl-N-(3-trifluoromethylphenyl)amide were added to a solution of 3.12 g (20 mmol) of 1-amidino-4,4-dimethyl-2-oxoimidazolidine in a mixture of 20 ml of tetrahydrofuran and 10 ml of methanol at 18–20° C., and the mixture was stirred at 20° C. for 1.5 hours. The solid which had separated out was then filtered off with suction. This and the resulting filtrate were worked up further in analogy to Example 1. 6.67 g (=81.7% yield) of product which, according to TLC, is virtually pure compound IV were obtained.

EXAMPLE 4

7.12 g (30 mmol) of 1-amidino-4,4-dimethyl-2-oxoimidazolidine hydrobromide were added to a mixture of 70 ml of 1-propanol and 5.5 ml of a 30% strength solution of sodium methylate in methanol (=30 mmol) at room temperature, and the mixture was stirred at room temperature for 20 min. Subsequently, at 20° C., 8.95 g (30 mmol) of 2-cyano-3-ethoxyacrylic acid N-methyl-N-(3-trifluoromethylphenyl)amide were added, and the mixture was stirred at 20° C. for 30 min and at 20°–25° C. for 1.5 hours. The solid which had separated out was then filtered off with suction, washed with 1-propanol and with water and dried as described in Example 1. The original filtrate was worked up as in Example 1. 6.82 g (=55.7% yield) of, according to TLC, virtually pure compound IV were obtained.

EXAMPLE 5

4.74 g (20 mmol) of 1-amidino-4,4-dimethyl-2-oxoimidazolidine hydrobromide were dissolved in 47 ml of boiling 1-propanol and, at 88°–90° C., 3.60 g (=3.67 ml, 20 mmol) of a 30% strength solution of sodium methylate in methanol were added. The resulting suspension was cooled to 45° C., stirred at 45° C. for 30 min and then cooled to 20° C., and 5.97 g (20 mmol) of 2-cyano-3-ethoxyacrylic acid N-methyl-N-(3-trifluoromethylphenyl)amide were added at 20° C., and the mixture was stirred at room temperature for 1.8 hours. The solid which had separated out was, after dilution of the pasty mass with 50 ml of ether, filtered off with suction and washed with ether. This product (initial crystals) and the residue from the original filtrate (mother liquor) were worked up further as described in Example 1 and dried. 6.23 g (=76.3% yield) of, according to TLC, virtually pure compound IV were obtained.

EXAMPLE 6

3.60 g (=3.67 ml, 20 mmol) of 30% strength $NaOCH_3$/ $CH_3OH$ solution were added to a solution of 4.74 g (20 mmol) of 1-amidino-4,4-dimethyl-2-oxoimidazolidine hydrobromide in 47 ml of methanol at room temperature, and the mixture was stirred at 45° C. for 30 min. The solution was then cooled to 20° C. and, at 20° C., 5.97 g (20 mmol) of 2-cyano-3-ethoxyacrylic acid N-methyl-N-(3-trifluoromethylphenyl)amide were added and the mixture was stirred at 20° C. for 20 min, at room temperature for 1.5 hours and while cooling in an icebath for 30 min. The solid which had separated out was filtered off with suction, washed with ether and worked up further as described in Example 1. Likewise, the residue from the filtrate (mother liquor) was further worked up as described in Example 1 and dried. 6.35 g (=77.7% yield) of, according to TLC ($CH_2Cl_2$/ $C_2H_5OH$=10:1), virtually pure compound IV were obtained.

It is possible in an analogous manner to employ in place of the hydrobromide used here the hydrochloride of 1-amidino-4,4-dimethyl-2-oxoimidazolidine (20 mmol= 3.85 g).

EXAMPLE 7

3.1 ml of a 6.6 molar solution of HCl in ether were added dropwise to a suspension of 8.17 g (20 mmol) of 1-cyano-1-[N-methyl-N-(3-trifluoromethylphenyl)carbamoyl]-2-[imino(4,4-dimethyl-2-oxo-1-imidazolidinyl)methylamino]

-ethene (compound IV) in 48 ml of ethanol at room temperature, and the mixture was stirred at 1°–3° C. for 1 hour. The solid was then filtered off with suction, washed with ether and dried at room temperature in vacuo (4–6 mbar) for 20 hours. 8.34 g (=90.7% yield) of pure 1-cyano-1-|N-methyl-N-(3-trifluoromethylphenyl)carbamoyl|-2-|imino-(4,4-dimethyl-2-oxo-1-imidazolidinyl) methylamino|ethene hydrochloride were obtained, melting point 180°–181° C. (=transition point; substance resolidifies); $C_{18}H_{20}ClF_3N_6O_2$ (444.86)

calculated: C 48.60 H 4.53 Cl 7.97 F 12.81 N 18.89%; found: C 48.20 H 4.35 Cl 8.0 F 12.75 N 18.60%

EXAMPLE 8

5 ml of a 0.5 molar solution of $HNO_3$ in ethyl acetate were added to a suspension of 1.00 g (2.45 mmol) of the compound IV in 6 ml of ethyl acetate at RT, and the mixture was stirred while cooling in an icebath for 3 hours. The solid was then filtered off with suction, washed with ethyl acetate and ether and dried at room temperature in vacuo (4 to 7 mbar) for 24 hours. 1.11 g ($\triangleq$ 94% yield) of pure nitrate of the compound IV were obtained, melting point 142° to 143° C.

$C_{18}H_{20}F_3N_7O_5$ (471.41); calculated: C 45.86 H 4.28 F 12.09 N 20.80%; found: C 46.3 H 4.6 F 12.0 N 21.1%

EXAMPLE 9

A solution of 1.634 g (4 mmol) of 1-cyano-1-[N-methyl-N-(3-trifluoromethylphenyl)carbamoyl]-2-[imino(4,4-dimethyl-2-oxo-1-imidazolidinyl)methylamino]ethene (compound IV) in 3 ml of formic acid (98–100% strength) was heated at 50° C. for 2 hours. The formic acid was then stripped off in vacuo, the residue was taken up in dichloromethane, 20 ml of water were added, and the pH was adjusted to between 9 and 10 with dilute sodium hydroxide solution. The organic phase was separated off. The aqueous phase was extracted twice more with dichloromethane. The combined dichloromethane extracts were washed successively with 2 ml of 0.5N NaOH and twice with water, dried with $MgSO_4$ and evaporated in vacuo. The remaining solid residue was mixed with ether/heptane 1:1 and filtered off with suction. After drying (compare Example 13), 0.93 g (=56.9% yield) of pure 4-amino-2-(4,4-dimethyl-2-oxo-1-imidazolidinyl)pyrimidine-5-carboxylic acid N-methyl-N-(3-trifluoromethylphenyl) amide was obtained, melting point 210°–211° C.; TLC in $CH_2Cl_2/C_2H_5OH=10:1$.

$C_{18}H_{19}F_3N_6O_2$ (408.40) (compound I); calculated: C 52.94 H 4.69 F 13.96 N 20.58%; found: C 52.8 H 5.0 F 13.4 N 20.4%

EXAMPLE 10

A solution of 3.268 g (8 mmol) of the compound IV in 6 ml of formic acid was heated at 40° C. for 3 hours and then worked up as described in Example 9. This resulted in 2.03 g (=62.1% yield) of compound I, melting point 210°–211° C.

EXAMPLE 11

A suspension of 1.634 g (4 mmol) of the compound IV in 3 ml of glacial acetic acid was stirred at 50° C. A solution had been produced after 1.5 hours and was further stirred at 50C for 1 hour and then diluted at room temperature with 25 ml of water and adjusted to pH 9 with 5.5 ml of 32% strength sodium hydroxide solution. The resulting mixture was extracted several times with ethyl acetate. The combined ethyl acetate extracts were washed twice with a little water, dried with $Na_2SO_4$, filtered and evaporated in vacuo. The residue was dissolved in 100 ml of $CH_2Cl_2$. This solution was extracted successively four times with 10 ml of 0.5N NaOH each time and twice with 4 ml of water each time, dried with $Na_2SO_4$, filtered and evaporated in vacuo. The residue was mixed with about 10 ml of ether at 2°–5° C. and filtered off with suction. Drying (as in Example 13) resulted in 1.26 g (=77.1% yield) of pure compound I, melting point 210.5°–211.5° C.

EXAMPLE 12

A mixture of 2.45 g (6 mmol) of the compound IV, 24 ml of tetrahydrofuran (THF) and 2.70 g (45 mmol) of glacial acetic acid was stirred while boiling under reflux, resulting in a solution after about 10 min, which was boiled under reflux for 3.8 hours and then evaporated in vacuo. The remaining residue was mixed with 8 ml of water and adjusted to pH 1 with 2N hydrochloric acid. The solid which then separated out was filtered off with suction, washed with ether and dried. This solid (0.68 g) was the compound VI formed as by-product. The acidic aqueous filtrate was adjusted to pH 9–10 with dilute sodium hydroxide solution, whereupon an oily product separated out and, on addition of a few ml of ether, crystallized. After cooling at 2°–4° C. for 1 hour, the crystals were filtered off with suction, washed with a little ether and dried as described in Example 13. 1.19 g (=48.6% yield) of pure compound I were obtained, melting point 210°–211° C.

EXAMPLE 13

A solution of 2.45 g (6 mmol) of the compound IV and 0.66 g (7.33 mmol) of anhydrous oxalic acid in 36 ml of absolute THF was boiled under reflux for 8 hours and then, at about 30° C., 34.5 ml of $CH_2Cl_2$ were added and the mixture was left to stand at RT for 17 hours. The crystalline substance which separated out was filtered off with suction, washed with a little $CH_2Cl_2$ and dried at 100° C. in vacuo (3–7 mbar). This resulted in 1.36 g of product which is the hydrogen oxalate of the compound I contaminated with oxalic acid. This product was dissolved in 5 ml of water, 2.3 ml of 2N NaOH were added, and the mixture was stirred while cooling in ice for 1 hour. The crystalline precipitate which separated out during this was filtered off with suction, washed with water and ether and dried at 100° C. in vacuo (180 mbar) for 17 h. 0.98 g (=40% yield) of the compound I was obtained, melting point 209°–210° C.

EXAMPLE 14

1.634 g (4 mmol) of the compound IV were added to a mixture of 20 ml of methanol and 0.392 g (~4 mmol) of concentrated sulfuric acid at room temperature, and the resulting solution was boiled under reflux for 9.5 hours. It was then evaporated in vacuo. The remaining residue was mixed with about 10 ml of water and adjusted to pH 9 with dilute sodium hydroxide solution. The mixture was extracted several times with ether. The collected ether extracts were washed with a little water, dried with $Na_2SO_4$, filtered and evaporated in vacuo. The remaining residue was triturated with heptane/ether 1:1. The resulting crystals were filtered off with suction and dried as described in Example 13. 0.22 g (=13.5% yield) of pure compound I was obtained, melting point 210°–211° C.

EXAMPLE 15

A mixture of 2.45 g (6 mmol) of the compound IV, 180 mg (2 mmol) of oxalic acid and 5 ml of glacial acetic acid was heated at 50° C. while stirring, a solution being produced after 30 minutes. Stirring was continued at 50° C. for 2.5 hours, and then the glacial acetic acid was stripped off in vacuo. The residue was mixed with 30 ml of $CH_2Cl_2$ and 20 ml of water, the aqueous phase was adjusted to pH 9–10 with dilute NaOH, the phases were separated, and the aqueous was extracted three times more with $CH_2Cl_2$. The combined $CH_2Cl_2$ extracts were washed with water, dried over $MgSO_4$, filtered and evaporated in vacuo. The remaining residue was mixed with ether/heptane 1:1. The crystals were filtered off with suction, washed with ether/heptane 3:1 and dried in vacuo (4–6 mbar). 1.83 g (=74.7% yield) of virtually pure compound I were obtained, melting point 209°–210° C.

EXAMPLE 16

A suspension of 2.45 g (6 mmol) of the compound IV in a mixture of 4.60 ml of glacial acetic acid and 0.40 ml of water was stirred at 50° C. The result after 30' was a solution which was stirred at 50° C. for a further 2.5 hours and subsequently evaporated in vacuo. About 10 ml of water were added to the residue, the pH was adjusted to 9–10 with dilute NaOH, and this mixture was extracted several times with $CH_2Cl_2$. The $CH_2Cl_2$ extract was washed twice with a little water, dried over $Na_2SO_4$, filtered and evaporated in vacuo. The crystalline residue was stirred with about 10 ml of ether. After cooling in an icebath for 1 hour, the solid was filtered off with suction, washed with ether and dried as in EXAMPLE 13. 1.74 g (=71% yield) of pure compound I were obtained, melting point 210°–211° C.

EXAMPLE 17

A mixture of 2.45 g (6 mmol) of compound IV, 820 mg (5 mmol) of trichloroacetic acid and 4.25 ml of glacial acetic acid was stirred at 70° C. for 2 hours and subsequently evaporated in vacuo. The remaining residue was taken up in 100 ml of ethyl acetate and extracted successively twice each with 20 ml of 2N NaOH each time and 10 ml of water each time. The solution was dried over $MgSO_4$ and then filtered and evaporated in vacuo. The residue was dissolved in 25 ml of ether, whereupon crystals separated out. The mixture was stirred at room temperature for 30 minutes and then evaporated in vacuo. The crystalline residue was suspended in diisopropyl ether, filtered off with suction and dried in vacuo at 100° C. for 15 hours. 1.36 g (=55.5% yield) of pure 4-amino-2-(4,4-dimethyl-2-oxo-1-imidazolidinyl)-pyrimidine-5-carboxylic acid N-methyl-N-(3-trifluoromethylphenyl)amide were obtained, melting point 209°–210° C.

EXAMPLE 18

A suspension of 1.78 g (4 imol) of 1-cyano-1-[N-methyl-N-(3-trifluoromethylphenyl)carbamoyl]-2-[imino-(4,4-dimethyl-2-oxo-1-imidazolidinyl)methylamino]ethene hydrochloride in 20 ml of water was stirred at 80° C. The result after 1.5 hours was a clear aqueous phase from which lumps of an adherent mass had separated out. Stirring at 80° C. for a further 5.9 hours was followed by adjustment to pH 1 with dilute hydrochloric acid and filtration. The filtrate was adjusted to pH 9–10 with NaOH, whereupon a crystalline precipitate separated out. After stirring while cooling in ice for 1 hour, the solid was filtered off with suction, washed with water and ether and dried as in EXAMPLE 13. 0.47 g (=28.8% yield) of the compound I was obtained, melting point 209°–210° C.

EXAMPLE 19

10.74 g (26.3 mmol) of 1-cyano-1-[N-methyl-N-(3-trifluoromethylphenyl)carbamoyl]-2-[imino(4,4-dimethyl-2-oxo-1-imidazolidinyl)methylamino]ethene (compound IV) were placed in a flask which had been preheated to 190° C. and was closed with a distillation head. The substance was left, with magnetic stirring, at 190° C. for 5 minutes and at 190°–192° C. for 6 min. The apparatus was then evacuated and the 3-methylaminobenzotrifluoride formed as by-product was substantially removed by distillation under vacuum at a bath temperature of 189° C.–175° C. over the course of 10 min. The resulting brown molten mass was taken up in 100 ml of $CH_2Cl_2$, and this solution was extracted successively three times with 35 ml of 0.5N NaOH each time, twice with 20 ml of water each time and four times with 25 ml of 1N hydrochloric acid each time, the collected aqueous hydrochloric acid extracts were clarified with active carbon, filtered and adjusted to pH 9 with sodium hydroxide solution. The precipitate which separated out was taken up in $CH_2Cl_1$, and the aqueous phase was extracted once with $CH_2Cl_2$. The combined $CH_2Cl_2$ extracts were washed with water, dried over $MgSO_4$, filtered and evaporated in vacuo. The remaining amorphous residue was dissolved in ether, whereupon a crystalline substance separated out after a few minutes. This was filtered off with suction after a few hours and dried at 100° C. in vacuo (180 mbar) for 15 hours. This resulted in 3.83 g (=35.7% yield) of TLC-pure 4-amino-2-(4,4-dimethyl-2-oxo-1-imidazolidinyl)pyrimidine-5-carboxylic acid N-methyl-N-(3-trifluoromethylphenyl)amide (compound I), melting point 209°–210° C.

$C_{18}H_{19}F_3N_6O_2$ (408.40); calculated: C 52.94 H 4.69 F 13.96 N 20.58%; found: C 52.8 H 5.0 F 13.35N 20.4%; TLC in $CH_2Cl_2/C_2H_5OH=10:1$.

The aqueous alkali extract obtained on working up contains compound VI which is formed as by-product. The good solubility of the hydrochloride of the compound I in water makes possible the described mode of working up which comprises convenient and efficient removal of by-products in the isolation of compound I.

EXAMPLE 20

2.67 g (6 mmol) of 1-cyano-1-[N-methyl-N-(3-trifluoromethylphenyl)carbamoyl]-2-[imino(4,4-dimethyl-2-oxo-1-imidazolidinyl)methylamino]ethene hydrochloride are heated at 187°–189° C. under vacuum (4–6 mbar) for 10 min in a bath preheated to 190° C. After cooling, the solidified melt was mixed with 5 ml of 2N sodium hydroxide solution. 12 ml of diethyl ether/diisopropyl ether 5:1 were added. Stirring resulted in initial formation of two clear phases, from which crystals separated out. The mixture was stirred while cooling in ice for 1 hour, and the crystals were filtered off with suction, washed with water and taken up in 50 ml of $CH_2Cl_2$. The solution which formed was extracted successively three times with 5 ml of 0.5N NaOH each time and twice with 5 ml of water each time, dried over $Na_2SO_4$, filtered and evaporated. The residue was triturated with diisopropyl ether, filtered off with suction and dried as in Example 13. 0.82 g (=32.6% yield) of the compound I was obtained, melting point 209°–210° C.

EXAMPLE 21

4N hydrochloric acid was added dropwise to a stirred suspension of 45.5 g (111.4 mmol) of 4-amino-2-(4,4-dimethyl-2-oxo-1-imidazolidinyl)pyrimidine-5-carboxylic acid N-methyl-N-(3-trifluoromethylphenyl)amide (compound I) in 810 ml of 1,2-dimethoxyethane at room temperature until the pH was constant at 3.0. 28.4 ml of 4N hydrochloric acid were required for this. The resulting solution was stirred for 30 min (at room temperature) and then evaporated in vacuo. The remaining viscous oily residue was dissolved in 150 ml of boiling acetone, whereupon the formation of a crystalline precipitate immediately started. After cooling in an icebath for 30 min, the crystals were filtered off with suction, washed with acetone and ether and dried at 100° C. in vacuo (180 mbar) for 17 hours. 46.7 g (=94.2% yield) of pure 4-amino-2-(4,4-dimethyl-2-oxo-1-imidazolidinyl)pyrimidine-5-carboxylic acid N-methyl-N-(3-trifluoromethylphenyl)amide hydrochloride were obtained, melting point 210°–211° C.

$C_{18}H_{20}ClF_3N_6O_2$ (444.86); calculated: C 48.60 H 4.53 Cl 7.97 F 12.81N 18.89%; found: C 48.4 H 4.4 Cl 7.8 F 12.0N 18.8%

The solubility of this hydrochloride of the compound I in water is indicated in Table 2 (No. 1).

EXAMPLE 22

1.5 ml of a 6.6 molar solution of HCl in ether were added dropwise to a solution of 3.68 g (9 mmol) of 2-amino-2-(4,4-dimethyl-2-oxo-1-imidazolidinyl)pyrimidine-5-carboxylic acid N-methyl-N-(3-trifluoromethylphenyl)amide in 20 ml of acetone at room temperature, the resulting suspension was stirred while cooling in an icebath for 30 min, and the crystalline solid was filtered off with suction. The latter was dried as described in Example 13. 3.75 g (93.7% yield) of pure 4-amino-2-(4,4-dimethyl-2-oxo-1-imidazolidinyl)pyrimidine-5-carboxylic acid N-methyl-N-(3-trifluoromethylphenyl)amide hydrochloride were obtained, melting point 210°–211° C.

EXAMPLE 23

In an analogous manner to the description in Example 22, 1.35 ml of a 6.6 molar solution of HCl in ether were added to a solution of 8 mmol of the compound I in 25 ml of ethyl acetate and 5 ml of methanol, and the mixture was then evaporated in vacuo. The viscous oily residue was dissolved in 20 ml of boiling acetone, whereupon a crystalline precipitate separated out after a few minutes. After stirring while cooling in an icebath for 30 min, the solid was filtered off with suction, washed with acetone and ether and dried as described in Example 13. 3.28 g (92.3% yield) of pure 4-amino-2-(4,4-dimethyl-2-oxo-1-imidazolidinyl)pyrimidine-5-carboxylic acid N-methyl-N-(3-trifluoromethylphenyl)amide hydrochloride were obtained, melting point 210°–211° C.

EXAMPLE 24

9.3 ml of a 0.5 molar solution of $HNO_3$ in ethyl acetate were added to a stirred suspension of 1.84 g (4.5 mmol) of compound I in 30 ml of ethyl acetate at room temperature. This resulted briefly in a solution, from which a crystalline precipitate separated out immediately and, after stirring at room temperature for 2 hours, was filtered off with suction and washed with ethyl acetate.

Drying of the crystals at 80° C. in vacuo (5 mbar) for 17 hours resulted in 2.02 g (95.2% yield) of pure 4-amino-2-(4,4-dimethyl-2-oxo-1-imidazolidinyl)pyrimidine-5-carboxylic acid N-methyl-N-(3-trifluoromethylphenyl)amide nitrate, melting point 220°–221° C.

$C_{18}H_{20}F_3N_7O_5$ (471.41); calculated: C 45.86 H 4.28 F 12.09N 20.80%; found: C 45.85 H 4.25 F 12.45N 20.90%

The solubility of this nitrate of the compound I in water is indicated in Table 2 (No. 2).

EXAMPLE 25

A solution of 285.5 mg (1.5 mmol) of p-toluenesulfonic acid hydrate in 10 ml of acetonitrile was added to a suspension of 613 mg (1.5 mmol) of compound I in 4 ml of acetonitrile at room temperature. The resulting solution (pH 3–4) was stirred at room temperature for 20 min and evaporated in vacuo. Ether was added to the residue. This resulted in crystallization of a substance which, after stirring at room temperature for 20 min, was filtered off with suction and washed with ether. Drying (5–6 mbar, 80° C., 8 hours) resulted in 820 mg (=94.1% yield) of pure 4-amino-2-(4,4-dimethyl-2-oxo-1-imidazolidinyl)pyrimidine-5-carboxylic acid N-methyl-N-(3-trifluoromethylphenyl)amide p-toluenesulfonate, melting point 168°–170° C.

$C_{25}H_{27}F_3N_6O_5S$ (580.61); calculated: C 51.72 H 4.68 F 9.82N 14.48 S 5.52%; found: C 51.3 H 4.7 F 10.0N 14.25 S 5.7%

The solubility of this p-toluenesulfonate of the compound I in water is indicated in Table 2 (No. 3).

EXAMPLE 26

A solution of 150.5 mg (1 mmol) of (R,R)-(+)-tartaric acid in 3 ml of methanol was added to a suspension of 408.5 mg (1 mmol) of 4-amino-2-(4,4-dimethyl-2-oxo-1-imidazolidinyl)pyrimidine-5-carboxylic acid N-methyl-N-(3-trifluoromethylphenyl)amide in 5 ml of acetonitrile at room temperature, whereupon a solution was produced. This was evaporated in vacuo at a bath temperature of 40° C. The remaining amorphous residue was dissolved in ether/acetonitrile 10:1. Crystals separated out after a few minutes. The mixture was stirred at room temperature for 2 hours and while cooling in an icebath for 1 hour, and the crystals were filtered off with suction, washed with ether and dried at 85° C. in vacuo (4–5 mbar). 510 mg (=91.3% yield) of 4-amino-2-(4,4-dimethyl-2-oxo-1-imidazolidinyl)pyrimidine-5-carboxylic acid N-methyl-N-(3-trifluoromethylphenyl)amide hydrogen (R,R)-tartrate were obtained, melting point 152°–153° C. (decomposition).

$C_{22}H_{25}F_3N_6O_8$ (558.49); calculated: C 47.31 H 4.51 F 10.21 N 15.05%; found: C 46.70 H 4.40 F 9.65 N 14.1%

The solubility of this hydrogen tartrate of the compound I in water is indicated in Table 2 (No. 4).

EXAMPLE 27

Production of a film-coated tablet with the composition specified hereinafter:

| Constituents (per tablet) | Weight (mg) |
| --- | --- |
| 1. 4-Amino-2-(4,4-dimethyl-2-oxo-1-imidazolidinyl)pyrimidine-5-carboxylic acid N-methyl-N-(3-tri-fluoromethylphenyl)amide hydrochloride | 100 |
| 2. Lactose | 35 |
| 3. Corn starch | 20 |
| 4. Microcrystalline cellulose | 10 |
| 5. Starch sodium glycolate | 8 |
| 6. Silicon dioxide | 5 |
| 7. Magnesium stearate | 2 |
| 8. Film coating | 10 |
| Total weight | 190 | a) Substances 1.–4. are mixed, compacted and passed through a Frewitt screen (mesh width 1.0 mm).
b) The granules from a) are dusted with substances 5.–7. and compressed.
c) The tablets from b) are coated with aqueous film coating.

EXAMPLE 28

Production of a film-coated tablet with the composition specified hereinafter:

| Constituent (per tablet) | Weight (mg) |
|---|---|
| 1. 4-Amino-2-(4,4-dimethyl-2-oxo-1-imidazolidinyl)pyrimidine-5-carboxylic acid N-methyl-N-(3-trifluoromethylphenyl)amide hydrochloride | 100 |
| 2. Lactose | 11 |
| 3. Hydroxypropylmethylcellulose | 60 |
| 4. Microcrystalline cellulose | 7 |
| 5. Magnesium stearate | 2 |
| 6. Film coating | 10 |
| Total weight | 190 | a) Substances 1.–4. are mixed, compacted and passed through a Frewitt screen (mesh width 1.0 mm).
b) The granules from a) are dusted with substance 5. and compressed.
c) The tablets from b) are coated with aqueous film coating.

This type of tablet is a composition with delayed release of active substance.

We claim:

1. A water soluble or water freely soluble physiologically tolerable acid addition salt of a compound of the formula selected from the group consisting of:

a. 4-amino-2-(4,4-dimethylmidazolidin-2-on-1-yl)pyrimidine-5-carboxylic acid N-methyl-N-(3-trifluoromethylphenyl)amide hydrochloride;

b. 4-amino-2-(4,4-dimethylimidazolidin-2-on-1-yl)primidine-5-carboxylic acid N-methyl-N-(3-trifluoromethylphenyl)amide hydrobromide;

c. 4-amino-2-(4,4-dimethylmidazolidin-2-on-1-yl)primidine-5-carboxylic acid N-methyl-N-(3-trifluoromethylphenyl)amide nitrate;

d. 4-amino-2-(4,4-dimethylimidazolidin-2-on-1-yl)primidine-5-carboxylic acid N-methyl-N-(3-trifluoromethylphenyl)amidehydrogen (R,R)-tartrate;

e. 4-amino-2-(4,4-dimethylimidazolidin-2-on-1-yl)primidine-5-carboxylic acid N-methyl-N-(3-trifluoromethylphenyl)amide para-toluenesulfonate.

2. A method of treating lipid metabolism disorders comprising administering to a mammal requiring lipid metabolism disorder treatment, a lipid metabolism disorder treatment effective amount of a water soluble or water freely soluble physiologically tolerable acid addition salt according to claim 1.

3. A lipid metabolism disorder treating composition comprising a lipid metabolism disorder treating effective amount of a water soluble or water freely soluble physiologically tolerable acid addition salt according to claim 1 and a carrier.

* * * * *

UNITED STATES PATENT AND TRADEMARK OFFICE
CERTIFICATE OF CORRECTION

PATENT NO. : 5,795,899
DATED : Aug. 18, 1998
INVENTOR(S) : Klaus-Dieter Kampe et al It is certified that error appears in the above-identified patent and that said Letters Patent is hereby corrected as shown below:

Claim 1, Column 28, Line 4, "dimethylmidazolidin" should read --dimethylimidizolidin--

Signed and Sealed this

Seventh Day of September, 1999

Attest:

Q. TODD DICKINSON

*Attesting Officer*  *Acting Commissioner of Patents and Trademarks*